United States Patent [19]

Kikuchi

[11] Patent Number: 4,998,973
[45] Date of Patent: Mar. 12, 1991

[54] ENDOSCOPE

[75] Inventor: Katsuya Kikuchi, Tochigi, Japan

[73] Assignee: Kabushiki Kaisha Toshiba, Kawasaki, Japan

[21] Appl. No.: 206,844

[22] Filed: Jun. 15, 1988

[30] Foreign Application Priority Data

Jun. 16, 1987 [JP] Japan ................. 62-147909

[51] Int. Cl.⁵ ........................ A61B 1/06; A61B 5/14
[52] U.S. Cl. ...................................... 128/6; 128/634; 356/41
[58] Field of Search ............. 128/4, 6, 633, 634; 358/98; 382/6; 356/41; 364/413.09

[56] References Cited

U.S. PATENT DOCUMENTS

| 3,690,769 | 9/1972 | Mori | 128/633 |
|---|---|---|---|
| 4,623,248 | 11/1986 | Sperinde | 128/634 |
| 4,651,741 | 3/1987 | Passafaro | 128/633 |
| 4,684,245 | 8/1987 | Goldring | 356/41 |
| 4,697,593 | 10/1987 | Evans et al. | 128/634 |
| 4,717,952 | 1/1988 | Kohayakawa et al. | 128/634 |
| 4,766,489 | 8/1988 | Kato | 128/6 X |
| 4,773,097 | 9/1988 | Suzaki et al. | 364/413.09 |
| 4,799,104 | 1/1989 | Hosoya et al. | 128/6 X |
| 4,807,026 | 2/1989 | Nishioka et al. | 128/6 X |
| 4,867,557 | 9/1989 | Takatani et al. | 128/633 |
| 4,878,113 | 10/1989 | Nakamura | 128/6 |

FOREIGN PATENT DOCUMENTS 151705 9/1986 Japan ................. 128/633

OTHER PUBLICATIONS

J. Hiramoto et al., "Tissue Spectrum Analyzer for Medical Use", Laser Research, vol. 13, No. 2, 1985, pp. 38–43.

Primary Examiner—William H. Grieb
Assistant Examiner—Jessica J. Harrison
Attorney, Agent, or Firm—Foley & Lardner

[57] ABSTRACT

An endoscope including a light source for generating light beams having difference wavelengths to an object in an internal organ such as the stomach and the intestines of a subject, in which picture signals are picked up by a pickup device such as an optoelectronic device from the object radiated with the light beams, in which correction signals such as reference picture signals for correcting sensitivities of the light source and the pickup device depending on the different wavelengths of the light beams are picked up by the pickup device from a reference member such as a reference white plate radiated with the same light beams, and in which a bloodstream amount and an oxygen saturation rate are operated from the picture signals and the correction signals. The bloodstream amount and the oxygen saturation rate may be displayed on a display. The correction signals may be picked up outside the body of the subject.

14 Claims, 3 Drawing Sheets

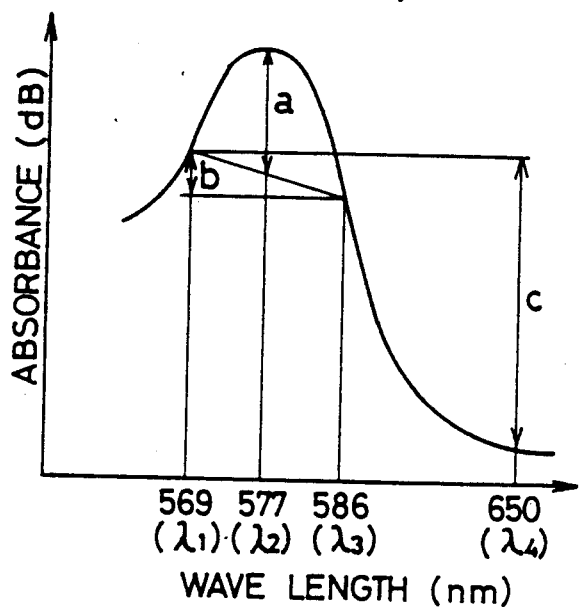
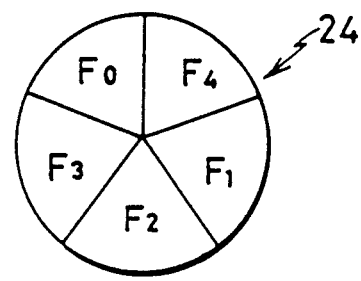
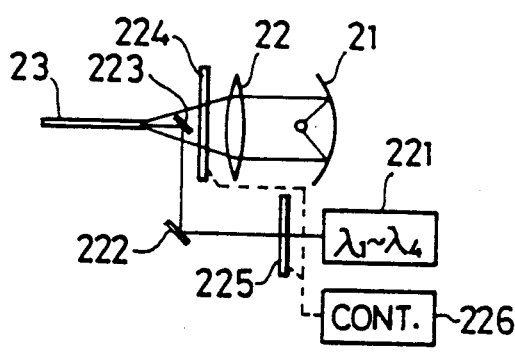
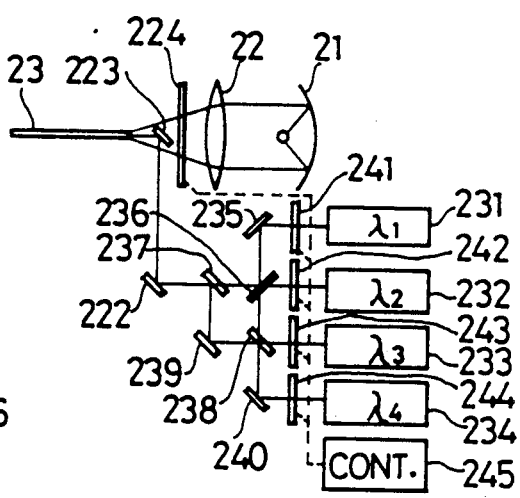
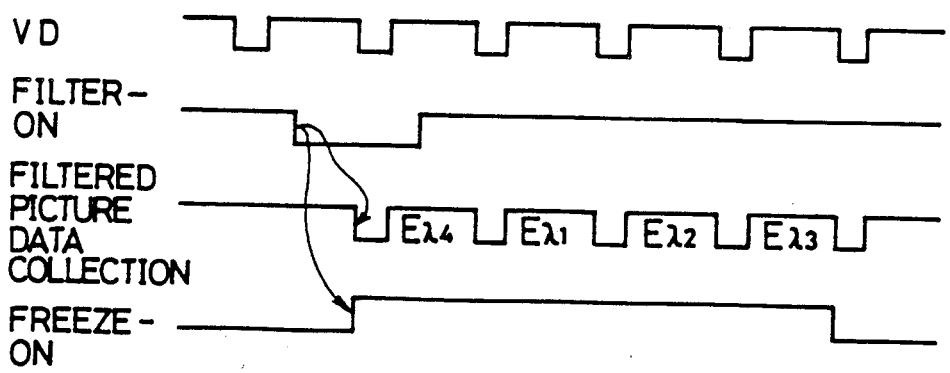

ENDOSCOPE

BACKGROUND OF THE INVENTION

1. Field of the Invention

The present invention relates to an endoscope and, more particularly, to an endoscope which is capable of obtaining functional information such as a bloodstream amount and an oxygen saturation rate by using picture data picked up by an optoelectronic device using light beams having different narrow-band wavelengths.

2. Description of the Prior Art

Recently, a variety of researches of a relation between a bloodstream state of a mucosa of an internal organ such as the stomach and the intestines of a subject and a disease thereof has been carried out in order to make clear the same, and a trial for utilizing measurements of functional information such as a bloodstream amount or a hemoglobin amount and an oxygen saturation rate by using a picture to conduct a diagnosis of a disease has been also carried out.

In the report titled to "SPECTRUM ANALYZER FOR MEDICAL TISSUE" of the literature "LASER RESEARCH", the 2nd number of the 13th volume, 1985, by Junichi HIRAMOTO and Masahiko KANDA, it is reported that a reflective spectrum of the mucosa of the stomach was measured to find certain relations between the bloodstream amount or the hemoglobin amount and the absorbance and between the oxygen saturation rate and the absorbance. In the report, there is shown in FIG. 1 an absorption spectrum of the hemoglobin in the blood of the human being, and in the drawing, at two points of wavelengths $\lambda_1$ of 569 nm and $\lambda_3$ of 586 nm, the spectrum values are not varied regardless of the variation of a ratio ($SO_2$) of the oxidized hemoglobin amount with reference to the whole hemoglobin amount, and thus the two points of the wavelengths $\lambda_1$ and $\lambda_3$ are fixed points. However, when the ratio $SO_2$ increases at a point of a wavelength $\lambda_2$ of 577 nm, the spectrum value increases, and, in turn, when the ratio $SO_2$ increases at a point of a wavelength $\lambda_4$ of 650 nm, the spectrum value decreases. Hence, taking advantage of these characteristics of the hemoglobin, by measuring values indicated by segments a, b and c of the absorption spectrum of FIG. 1, the bloodstream amount or the hemoglobin amount ($I_{HB}$) and the oxygen saturation rate ($I_{SO2}$) can be obtained in accordance with the following formulas:

$$I_{HB} = 200 \cdot c$$

and $$I_{SO2} = 0.673 \cdot a/b$$

In the conventional method, when the measurement of the spectrum described above is carried out from one point to another point over the surface of the mucosa, it takes a long time to examine the entire wide surface. In an endoscopic detection, in particular, such an examination method will give a subject person considerable pain, and the object such as the stomach and the intestines to be examined is always in motion by peristalsis or a heart pulsation. Therefore, this method is not practical. Accordingly, it has been desired to measure the distributions of the bloodstream amount and the oxygen saturation rate as two-dimensional picture information in a short time. However, the conventional endoscope has no such a device for measuring the bloodstream amount and the oxygen saturation rate in the short time.

SUMMARY OF THE INVENTION

Accordingly, it is an object of the present invention to provide an endoscope, free from the aforementioned disadvantages and defects of the prior art, which is capable of measuring functional information such as a bloodstream amount and an oxygen saturation rate by using picture data picked up by an optoelectronic device using light beams having different narrow-band wavelengths.

In accordance with one aspect of the present invention, there is provided an endoscope, comprising means for generating light beams having different wavelengths to an object of a subject, pickup means for picking up picture signals from the object using the light beams, correction means for correcting sensitivities of the light beam generating means, the pickup means and the correction means depending on the different wavelengths of the light beams to output correction signals, and operation means for operating a bloodstream amount and an oxygen saturation rate from the picture signals and the correction signals.

In accordance with another aspect of the present invention, there is provided an endoscope, comprising means for generating light beams having different wavelengths to an object of a subject, pickup means for picking up picture signals from the object using the light beams and for picking up correction signals from a reference member using the light beams for correcting sensitivities of the light beam generating means and the pickup means, and operation means for operating a bloodstream amount and an oxygen saturation rate from the picture signals and the correction signals.

BRIEF DESCRIPTION OF THE DRAWINGS

Above and other objects, features and advantages of the present invention will more fully appear from the following description of the preferred embodiments with reference to the accompanying drawings, in which:

FIG. 1 is a graphical representation of a conventional absorption spectrum of hemoglobin in the blood of the human being;

FIG. 4 is an elevation of an interference filter plate of the endoscope of FIG. 1;

FIG. 5 is a timing chart of signals for collecting a sequence of picture data of narrow-band wavelengths;

FIG. 6 is a schematic view of another embodiment of a light source portion used for the endoscope of FIG. 2; and FIG. 7 is a schematic view of still another embodiment of a light source portion used for the endoscope of FIG. 2.

DESCRIPTION OF THE PREFERRED EMBODIMENTS

Figure 2:
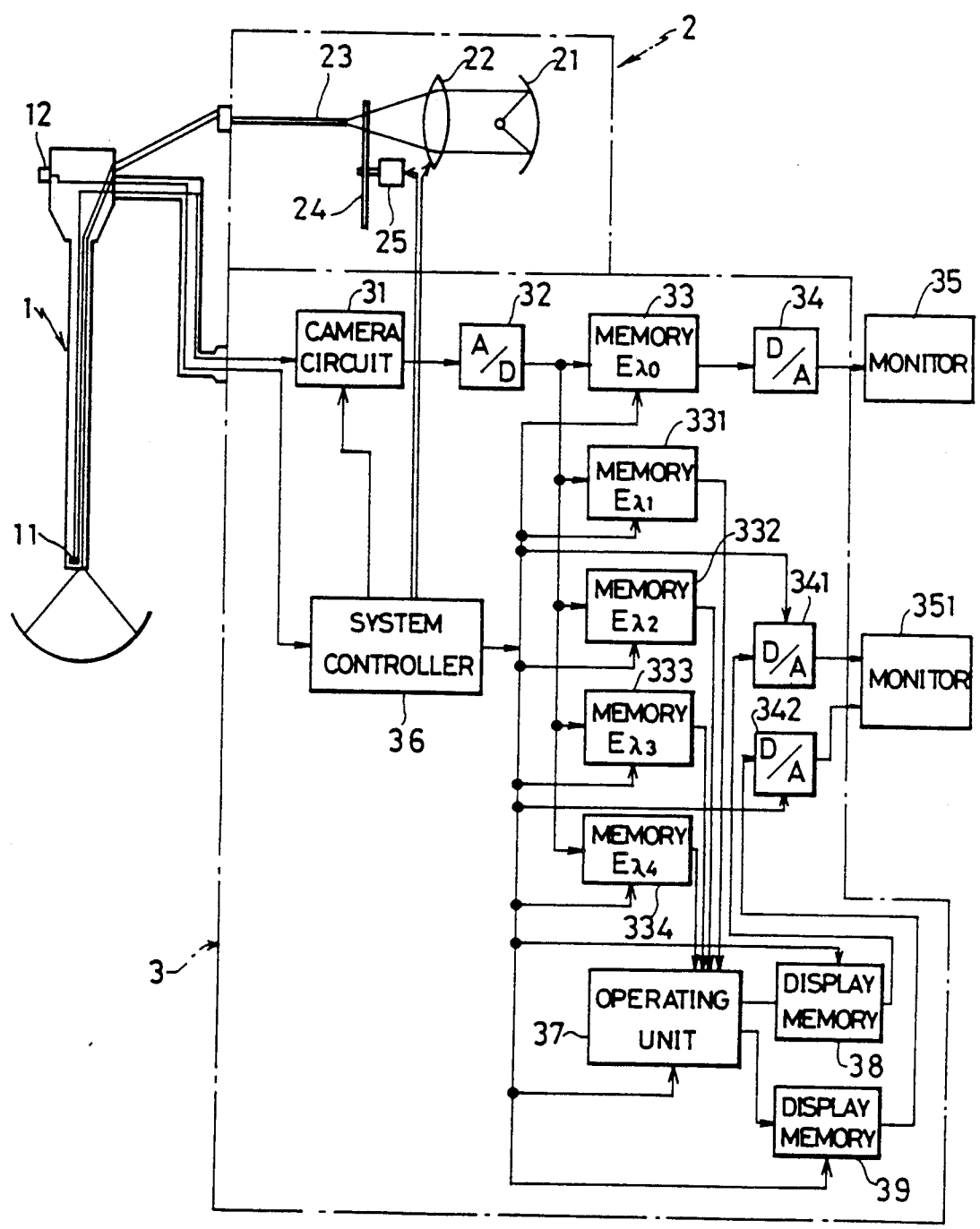
FIG. 2 is a schematic block diagram of one embodiment of an endoscope according to the present invention.

The present invention will now be described in detail with reference to its preferred embodiments in connection with the accompanying drawings, wherein like reference characters designate like or corresponding parts throughout the several views.

First, a principle of operation for obtaining a bloodstream amount and an oxygen saturation rate of a surface of an object in an internal organ, such as the stomach and the intestines, of a subject observed by an endoscope according to the present invention will be described.

The bloodstream amount and the oxygen saturation rate are operated from picture data $(E\lambda_i)$ and $(E\lambda_j)$, which can be obtained by photographing the object, such as the stomach and the intestines, using light beams having narrow-band wavelengths $\lambda_i$ and $\lambda_j$, wherein i and j are integers such as 1, 2, ..., and reference picture data $(Er\lambda_i)$ and $(Er\lambda_j)$, which can be obtained by photographing a reference white plate outside the body of an animal such as a human being, using the same light beams using the following formula, as hereinafter described in detail:

$$\log \frac{E\lambda_i}{E\lambda_j} + \log \frac{Er\lambda_j}{Er\lambda_i} \tag{1}$$

In this case, since the sensitivities of the light source for generating the light beams, a camera for photographing the object and the reference white plate and optical systems therefor depend on the wavelengths of the light beams, and thus the reference picture data $(Er\lambda_i)$ and $(Er\lambda_j)$ are required to correct the dependence of the different wavelengths, because the reflection intensity can be obtained using the reference white plate regardless of the wavelengths of the light beams. According to the present invention, it is not restricted to the reference white plate and, of course, another material having the same function as the reference white plate may be used.

An absorbance $A(\lambda)$ is expressed in the following formula:

$$A(\lambda) = -\log \frac{R(\lambda)}{Rr(\lambda)} \tag{2}$$

wherein $R(\lambda)$ is a reflection spectrum of the object and $Rr(\lambda)$ is a reflection spectrum of the reference white plate. When the object is photographed using a light beam having a narrow-band wavelength $\Delta\lambda$ by using a television camera, an output value $E_{80}$ of the camera is represented by the following formula:

$$E_\lambda = P(\lambda).R(\lambda).S(\lambda).\Delta\lambda \tag{3}$$

wherein $P(\lambda)$ is a spectrum distribution of the light source and $S(\lambda)$ is photographing characteristics of the camera. Then, when the reference white plate is photographed in the same manner as above by using the television camera, an output value $Er\lambda$ of the camera is expressed by the following formula:

$$Er_{80} = P(\lambda).Rr(\lambda).S(\lambda).\Delta\lambda \tag{4}$$

Then, formulas (3) and (4) are rewritten as follows:

$$R(\lambda) = \frac{E_\lambda}{P(\lambda) \cdot S(\lambda) \cdot \Delta\lambda}$$

$$Rr(\lambda) = \frac{Er_\lambda}{P(\lambda) \cdot S(\lambda) \cdot \Delta\lambda}$$

The relation between the reflection spectrum $R(\lambda)$ and $Rr(\lambda)$ and the outputs $E\lambda$ and $Er\lambda$ of the camera is expressed in the following formula:

$$R(\lambda) = \frac{E_\lambda}{Er_\lambda} \cdot Rr(\lambda) \tag{5}$$

From formulas (1)–(5), the relations between the output values of the camera and the bloodstream amount and between the output values of the camera and the oxygen saturation rate are led in connection with FIG. 1. As described hereinbefore, the bloodstream amount $I_{HB}$ and the oxygen saturation rate $I_{SO_2}$ are obtained in accordance with the following formulas:

$$I_{HB} = 200 \cdot c \tag{6}$$

and $$I_{SO_2} = 0.673 \cdot a/b \tag{7}$$

Firstly, the bloodstream amount $I_{HB}$ will be obtained. First, the value c of the formula (6) for obtaining the bloodstream amount is operated from the picture data as follows:

$$\begin{aligned}
c &= A(\lambda_1) - A(\lambda_4) \\
&= -\log \frac{R(\lambda_1)}{Rr(\lambda_1)} + \log \frac{R(\lambda_4)}{Rr(\lambda_4)} \\
&= \log \frac{R(\lambda_4)}{R(\lambda_1)} + \log \frac{Rr(\lambda_1)}{Rr(\lambda_4)}
\end{aligned} \tag{8}$$

Now, since $Rr(\lambda)$ hardly depends on the wavelength $\lambda$, an approximation of $Rf(\lambda_1) \approx Rr(\lambda_4)$ is substituted in the above formula, for example, $Rf(\lambda_1) = 0.992$ and $Rr(\lambda_4) = 0.990$. Then, formula (8) is expressed by the following formula:

$$c \approx \log \frac{R(\lambda_4)}{R(\lambda_1)} \tag{9}$$

Then, $$\frac{R(\lambda_4)}{R(\lambda_1)} = \frac{\frac{E_{\lambda_4}}{Er_{\lambda_4}} \cdot Rr(\lambda_4)}{\frac{E_{\lambda_1}}{Er_{\lambda_1}} \cdot Rr(\lambda_1)} \tag{10}$$

$$= \frac{E_{\lambda_4}}{E_{\lambda_1}} \cdot \frac{Er_{\lambda_1}}{Er_{\lambda_4}} \cdot \frac{Rr(\lambda_4)}{Rr(\lambda_1)}$$

$$\approx \frac{E_{\lambda_4}}{E_{\lambda_1}} \cdot \frac{Er_{\lambda_1}}{Er_{\lambda_4}}$$

From formulas (9) and (10), $$c = \log \frac{E_{\lambda_4}}{E_{\lambda_1}} + \log \frac{Er_{\lambda_1}}{Er_{\lambda_4}} \tag{11}$$

In formula (11), the first member is the ratio of the outputs of the camera when the object is photographed by using the light beams having the wavelengths $\lambda_4$ and $\lambda_1$, and the second member is the ratio of the outputs of the camera when the reference white plate is photographed outside the body by using the same light beams. Hence, the data obtained by photographing the reference white plate outside the body may be conveniently utilized.

Then, the bloodstream amount $I_{HB}$ is obtained by substituting the resulted value c in formula (6).

Secondly, the oxygen saturation rate $^{I}SO_2$ will be obtained. First, the value a/b of the formula (7) for obtaining the oxygen saturation rate is operated from the picture data as follows:

$$\frac{a}{b} = \frac{A(\lambda_2) - 0.45\{A(\lambda_1) - A(\lambda_3)\} - A(\lambda_3)}{A(\lambda_1) - A(\lambda_3)} \quad (12)$$

$$= \frac{0.45\{A(\lambda_2) - A(\lambda_1)\} + 0.55\{A(\lambda_2) - A(\lambda_3)\}}{A(\lambda_1) - A(\lambda_3)}$$

In formula (12), the difference formulas in the numerator and the denominator have the same forms as that of formula (8), and thus each of these difference formulas are expressed in the same form as formula (11) as follows:

$$\Delta A_{13} = A(\lambda_1) - A(\lambda_3) \approx \log\frac{E_{\lambda 3}}{E_{\lambda 1}} + \log\frac{E_{r\lambda 1}}{E_{r\lambda 3}} \quad (13)$$

$$\Delta A_{21} = A(\lambda_2) - A(\lambda_1) \approx \log\frac{E_{\lambda 1}}{E_{\lambda 2}} + \log\frac{E_{r\lambda 2}}{E_{r\lambda 1}} \quad (14)$$

$$\Delta A_{23} = A(\lambda_2) - A(\lambda_3) \approx \log\frac{E_{\lambda 3}}{E_{\lambda 2}} + \log\frac{E_{r\lambda 2}}{E_{r\lambda 3}} \quad (15)$$

Accordingly, by substituting formulas (13) to (15) in formula (12), the value a/b is expressed in the following formula:

$$\frac{a}{b} = \frac{0.45\Delta A_{21} + 0.55\Delta A_{23}}{\Delta A_{13}} \quad (16)$$

Then, the oxygen saturation rate $^{I}SO_2$ is obtained by substituting the resulted value a/b in formula (7).

In this case, as described above, the outputs of the camera, obtained by photographing the object and the reference white plate using the light beams having the three different wavelengths $\lambda_1$, $\lambda_2$, and $\lambda_3$, are operated in accordance with formulas (13)–(16) to obtain the oxygen saturation rate.

In the embodiment described above, when the operation of formula (11) is carried out, since the second member of formula (11) is a fixed value, the operation of formula (11) can be simplified to conduct according to the following formula:

$$c = \log E_{80\,4} - \log E_{80\,1} + b_0 \quad (17)$$

wherein $b_0$ is a fixed number. As to formulas (13)–(15), the second members thereof are fixed values, and hence the operation of formulas (13)–(15) can be simplified in the same manner as that of formula (11) to formula (17) as $$\Delta A_{13} = \log E_{80\,3} - \log E_{\lambda 1} + b_1 \ldots \quad (18)$$

$$\Delta A_{21} = \log E_{\lambda 1} - \log E_{\lambda 2} + b_2 \ldots \quad (19)$$

$$\Delta A_{23} = \log E_{\lambda 3} - \log E_{\lambda 2} + b_3 \ldots \quad (20)$$

wherein $b_1$, $b_2$ and $b_3$ are fixed numbers.

Then, the present invention will now be described in detail with reference to FIGS. 2 to 5.

In FIG. 2, there is shown one embodiment of an endoscope according to the present invention. The endoscope comprises a scope portion 1 for observing an inside of an internal organ such as the stomach and the intestines, a light source portion 2 for generating light beams having narrow-band wavelengths, and a system body portion 3 for operating a bloodstream amount and an oxygen saturation rate. The scope portion 1 includes an optoelectronic device 11 such as a charge coupled device (CCD) camera arranged in its end portion for photographing an object, and a button switch 12 for collecting images of the bloodstream amount and the oxygen saturation rate. The light source portion 2 includes a light source 21 such as a xenon lamp and the like, a condenser lens 22 for collecting the light, a light guide 23, an interference filter disc plate 24 for passing the light beams having the narrow-band wavelengths, and a step motor 25 for intermittently rotating the filter plate 24. The system body portion 3 includes a camera circuit 31 for driving the optoelectronic device 11 and converting output signals thereof into video signals, an analog-digital (A/D) converter 32 for converting the analog video signals output from the camera circuit 31 into digital video data, picture memories 33, 331, 332, 333 and 334 for storing digital picture data output from the A/D converter 32, a digital-analog (D/A) converters 34 for converting the digital picture data into analog picture signals, connected to the memory 33, a monitor 35 connected to the D/A converter 34, a system controller 36 for controlling the scope portion 1, the light source portion 2 and the system body portion 3, an operating unit 37 connected to the memories 331, 332, 333 and 334, two display memories 38 and 39 connected to the operating unit 37, two D/A converters 341 and 342 connected to the display memories 38 and 39, respectively, and another monitor 351 connected to the D/A converters 341 and 342.

In FIG. 4, there is shown one example of the interference filter disc plate 24 including one transparent filter member $F_0$ for obtaining a white light beam and four interference filter members $F_1$, $F_2$, $F_3$ and $F_4$. The four filter members $F_1$, $F_2$, $F_3$ and $F_4$ may pass the light beams having main narrow-band wavelengths $\lambda_1$, $\lambda_2$, $\lambda_3$ and $\lambda_4$, for instance, 569 nm, 577 nm, 586 nm and 650 nm, respectively.

Figure 3:
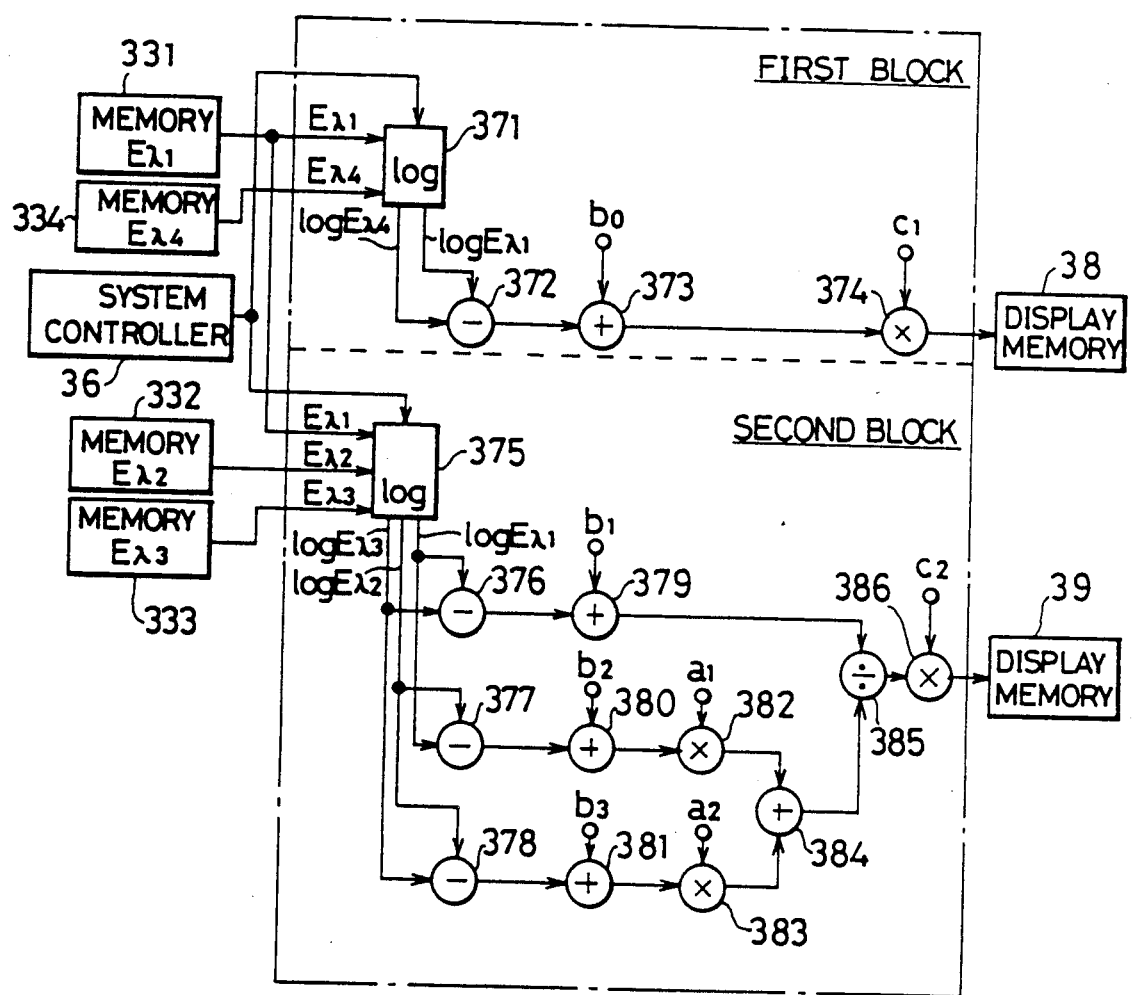
FIG. 3 is a block diagram of a processing unit of the endoscope of FIG. 1.

In FIG. 3, there is shown one embodiment of the operating unit 37 comprising first and second blocks for operating the bloodstream amount and the oxygen saturation rate, respectively. The first block includes a logarithmic operational circuit 371 connected to the picture memories 331 and 334, a subtracter 372 connected to the logarithmic operational circuit 371, an adder 373 connected to the subtracter 372, and a multiplier 374 connected to the adder 373 and outputting a signal corresponding to the bloodstream amount to the display memory 38. The second block includes a logarithmic operational circuit 375 connected to the picture memories 331, 332 and 333, three subtracters 376, 377 and 378 connected to the logarithmic operational circuit 375, three adders 379, 380 and 381 connected to the subtracters 376, 377 and 378, respectively, two multipliers 382 and 383 connected to the adders 380 and 381, respectively, another adder 384 connected to the multipliers 382 and 383, a divider 385 connected to the adders 379 and 384, and a multiplier 386 connected to the divider 385 and outputting a signal corresponding to the oxygen saturation rate to the display memory 39. A plurality of fixed values $a_1$, $a_2$, $b_0$, $b_1$, $b_2$, $b_3$, $c_1$ and $c_2$, as described hereinbelow, are fed to the multiplier 382, the multiplier 383, the adder 373, the adder 379, the adder 380, the adder 381, the multiplier 374 and multiplier 386, respectively.

$a_1 = 0.45;$ $a_2 = 0.55;$ $b_0 = \log({}^E\lambda_1/{}^E\lambda_4);$ $b_1 = \log({}^E\lambda_1/{}^E\lambda_3);$ $b_2 = \log({}^E\lambda_2/{}^E\lambda_1);$ $b_3 = \log({}^E\lambda_2/{}^E\lambda_3);$ $c_1 = 200;$ and $c_2 = 0.673.$ The logarithmic operational circuits 371 and 375 are controlled by the system controller 36.

Then, the operation of the endoscope according to the present invention will be described with reference to FIGS. 2 and 3.

When the object such as the stomach and the intestines is observed by the endoscope, the transparent filter member $F_0$ of the filter disc plate 24 is selected by the step motor 25 according to a control signal of the system controller 36. The camera 11 photographs the object to pick up picture signals, and the picture signals are converted into the digital picture data in the A/D converter 32, and the digital picture data is stored in the memory 33. The digital picture data read out of the memory 33 is converted into the analog video signals in the D/A converter 34, and the analog video signals are fed to the monitor 35 for momentarily displaying the picture of the object on the monitor 35.

Now, the button switch 12 for collecting the bloodstream amount and the oxygen saturation rate is pushed on, and the filter disc plate 24 is intermittently rotated by the step motor 25 according to the control signal output from the system controller 36 in order to select the filter members $F_4$, $F_1$, $F_2$ and $F_3$, in order. In synchronization with the selection of the filter members $F_4$, $F_1$, $F_2$ and $F_3$, filtered analog picture signals are picked up by the camera 11 and are converted into the filtered digital picture data ${}^E\lambda_4$, ${}^E\lambda_1$ and ${}^E\lambda_2$ and ${}^E\lambda_3$ in order in the A/D converter 32, and the filtered digital picture data ${}^E\lambda_4$, ${}^E\lambda_1$, ${}^E\lambda_2$ and ${}^E\lambda_3$ is then stored in the picture memories 334, 331, 332 and 333, respectively. At this time, the picture data picked up just before the button switch 12 is pushed on is frozen in the picture memory 33 while the picture represented by the frozen picture data is displayed on the monitor 35. Soon after finishing the storing of the filtered digital picture data ${}^E\lambda_1$, ${}^E\lambda_2$, ${}^E\lambda_3$ and ${}^E\lambda_4$ into the picture memories 331, 332, 333 and 334, a normal picture is displayed again at the real time on the monitor 35.

Then, the picture data ${}^E\lambda_1$, ${}^E\lambda_2$, ${}^E\lambda_3$ and ${}^E\lambda_4$ stored in the picture memories 331, 332, 333 and 334 is read out thereof and is operated in the operating unit 37 of FIG. 3 in order to obtain the bloodstream amount and the oxygen saturation rate by the control signals output from the system controller 36 in accordance with formulas (6), (7), and (16) to (20) as follows.

As shown in FIG. 3, the picture memories 331, 332, 333 and 334 output the respective picture data ${}^E\lambda_1$, ${}^E\lambda_2$, ${}^E\lambda_3$ ${}^E\lambda_4$ to the logarithmic operational circuits 371 and 375. The logarithmic operational circuit 371 receives the picture data ${}^E\lambda_1$ and ${}^E\lambda_4$ operates log ${}^E\lambda_E$ and log ${}^E\lambda_4$. The subtracter 372 calculates log ${}^E\lambda_4 - \log {}^E\lambda_1$ and outputs this subtraction result to the adder 373, and the adder 373 adds the fixed value $b_0$ to the subtraction result to output the obtained value c of formula (17) to the multiplier 374. The multiplier 374 multiplies the value c by the fixed value $c_1$ to obtain the bloodstream amount 200.c of formula (6) and outputs this result to the display memory 38.

Then, the logarithmic operational circuit 375 receives the picture data ${}^E\lambda_1$, ${}^E\lambda_2$ and ${}^E\lambda_3$ and operates log ${}^E\lambda_1$, log ${}^E\lambda_2$ and log${}^E\lambda_3$. The subtracter 376 calculates log ${}^E\lambda_3 - \log{}^E\lambda_1$ and outputs the subtraction result to the adder 379, and the adder 379 adds the fixed value $b_1$ to the subtraction result to output the addition result to the divider 385. The subtracter 377 calculates log ${}^E\lambda_1 - \log {}^E\lambda_2$ and outputs the subtraction result to the adder 380, and the adder 380 adds the fixed value $b_2$ to the subtraction result to output the addition result to the multiplier 382. The multiplier 382 multiplies the addition result by the fixed value $a_1$ and outputs the multiplication result to the adder 384. The subtracter 378 calculates log ${}^E\lambda_3 - \log {}^E\lambda_2$ and outputs the subtraction result to the adder 381, and the adder 381 adds the fixed value $b_3$ and outputs the addition result to the multiplier 383. The multiplier 383 multiplies the addition result by the fixed value $a_2$ to output the multiplication result to the adder 384. The adder 384 adds the multiplication results of the multipliers 382 and 383 and outputs the addition result to the divider 385, and the divider 385 divides the addition result of the adder 384 by the addition result of the adder 379 to output the value a/b of formula (16) to the multiplier 386. The multiplier 386 multiplies the value a/b by the fixed value $c_2$ to obtain the oxygen saturation rate 0.637.a/b of formula (7) and outputs this result to the display memory 39.

The obtained bloodstream amount and oxygen saturation rate are stored in the display memories 38 and 39, respectively, and then are read out of the display memories 38 and 39 by the control signals output from the system controller 36. The readout values are fed to the D/A converters 341 and 342, respectively, and are converted into the analog signals therein by the control signals output from the system controller 36, and the converted analog signals are alternatively fed to the monitor 351 for alternatively displaying the bloodstream amount and the oxygen saturation rate thereon.

In FIG. 5, there is shown a timing chart of vertical drive (VD) pulses of the video signal, a filter-on signal, a filtered picture data collecting signal and a freeze-on signal for a sequence for collecting the picture data of the narrow-band wavelengths. When the button switch 12 for collecting the bloodstream amount and the oxygen saturation rate is pushed on, the filter-on pulse is output as a negative logical pulse from the controller 36 to the camera circuit 31. The collection of the filtered picture signals ${}^e\lambda_4$, ${}^E\lambda_1$, ${}^E\lambda_2$ and ${}^E\lambda_3$ is triggered by a trailing edge of the filter-on pulse at the timing of the trailing edge thereof, and the filtered picture signals ${}^E\lambda_4 {}^E\lambda_1$, ${}^E\lambda_2$ and ${}^E\lambda_3$ are collected by the filtered picture data collecting signal in synchronization with the vertical drive pulses of the video signal while the picture data stored in the picture memory 33 is frozen by the freeze-on signal output from the controller 36.

In FIG. 6, there is shown another embodiment of the light source portion. In this embodiment, the light source portion includes a light source 21, a condenser lens 22 and a light guide 23 in the same manner as those of the light source portion 2 shown in FIG. 2, and further includes a variable wavelength laser tube 221 which is capable of generating light beams having different narrow-band wavelengths $\lambda_1$, $\lambda_2$, $\lambda_3$ and $\lambda_4$, two total reflection mirrors 222 and 223 for reflecting the light beams generated by the laser tube 221 to the light guide 23, two shutters 224 and 225 arranged in front of the condenser lens 22 and the laser tube 221, respectively, for shutting out the light beams generated thereby, and a shutter controller 226 for controlling the open and close of the shutter 224 and 225. In this case, when the white light beam is generated, the shutter 224 is opened and the shutter 225 is closed by operating the shutter controller 226. When the light beams having the wavelengths $\lambda_1$, $\lambda_2$, $\lambda_3$ and $\lambda_4$ are generated, the shutter 224 is closed. Then, the light beams having the wavelengths $\lambda_1$, $\lambda_2$, $\lambda_3$ and $\lambda_4$ are generated in order by the laser tube 221 while the shutter 225 is opened.

In FIG. 7, there is shown still another embodiment of the light source portion. In this embodiment, the light source portion includes a light source 21, a condenser lens 22 and a light guide 23 in the same manner as those of the light source portion 2 shown in FIG. 2, and further includes four laser tubes 231, 232, 233 and 234 for generating light beams having different narrow-band wavelengths $\lambda_1$, $\lambda_2$, $\lambda_3$ and $\lambda_4$, respectively, total reflection mirrors 222, 223, 235, 239 and 240 and half reflection mirrors 236, 237 and 238 for reflecting the light beams generated by the laser tubes 231 to 234 to the light guide 23, five shutters 224, 241, 242, 423 and 244 shutters arranged in front of the condenser lens 22 and the laser tubes 231, 232, 233 and 234, respectively, for shutting out the light beams generated thereby, and a shutter controller 245 for controlling the open and close of the shutters 224, 231, 232, 233 and 234. In this case, when the white light beam is generated, the shutter 224 is opened and the other shutters 241 to 244 are closed by the shutter controller 245. When the light beams having the wavelengths $\lambda_1$, $\lambda_2$, $\lambda_3$ and $\lambda_4$ are generated, the laser tubes 231 to 234 are driven to generate the respective light beams and one of the shutters 241 to 244 is consecutively opened in order while the other shutters are closed by operating the shutter controller 245.

In the preferred embodiment, although the bloodstream amount and the oxygen saturation rate are alternatively displayed on the monitor, of course, they may be displayed in the left and right halves or the upper and lower halves of the display surface of the monitor at the same time, or only one of them may be displayed on the monitor. Further, although the normal picture and the bloodstream amount or the oxygen saturation rate are separately displayed on the two monitors, they may be alternately displayed on one monitor, or may be displayed in the left and right halves or the upper and lower halves of the display surface of one monitor at the same time. Further, the bloodstream amount or the oxygen saturation rate may be displayed in the desired color, placing over the normal frozen picture.

Further, although the bloodstream amount and the oxygen saturation rate have been described in the preferred embodiment, however, it is readily understood that an image of an absorbance of an object can be formed by operating picture data picked up by photographing the object using light beams having different wavelengths, in the same manner as described above.

It is readily understood from the above description of the preferred embodiment that the two-dimensional picture information such as the distributions of the bloodstream amount or the hemoglobin amount and the oxygen saturation rate of the surface of the object of the internal organs such as the stomach and the intestines can be quickly realized to the images in the endoscope according to the present invention. Therefore, the disadvantages such as the pain given to the subject person of the endoscope can be largely reduced, and the influences due to the peristalsis of the stomach or the intestines and the pulsation of the heart can be disregarded. Further, the functional information such as the bloodstream amount or the hemoglobin amount and the oxygen saturation rate of the mucosa of the internal organ such as the stomach and the intestines can be obtained, and thus the effects of the diagnosis using the endoscope can be largely raised. For instance, a discrimination of a diseased part concentrated with blood, like a cancer, can be readily performed, and hence it is expected to contribute to an early detection of the cancer.

Further, according to the present invention, the reference picture data for correcting the dependence of the wavelengths, obtained by photographing the reference white plate outside the body can be conveniently used, which is a great advantage in practice.

Although the present invention has been described in its preferred embodiment with reference to the accompanying drawings, it is readily understood that the present invention is not restricted to the preferred embodiment and that various changes and modifications may be made in the present invention by a person skilled in the art without departing from the spirit and scope of the present invention.

What is claimed is:

1. An endoscope, comprising:
   means for generating light beams of different wavelengths toward an object;
   pickup means for picking up picture signals from the object by using the light beams, and also picking up correction signals from a reference member by using the light beams; and
   calculation means for calculating a bloodstream amount $I_{HB}$ and an oxygen saturation rate $I_{SO_2}$ from the picture signals and the correction signals according to formulas (1), (2) and (3) below, $$\Delta A_{ij} = \log \frac{E\lambda i}{E\lambda j} + \log \frac{Er\lambda j}{Er\lambda i} \tag{1}$$

wherein $E\lambda i$ and $E\lambda j$ are the picture signals and $Er\lambda i$ and $Er\lambda j$ are reference picture signals as the correction signals, wherein $\lambda i$ and $\lambda j$ are wavelengths and wherein $i$ and $j$ are integers $1, 2, 3, 4, \ldots$ $$I_{HB} = 200 \, \Delta A_{14} \ldots \tag{2}$$

$$I_{SO_2} = 0.673 \cdot \left( \frac{0.45 \cdot \Delta A_{21} + 0.55 \cdot \Delta A_{23}}{\Delta A_{13}} \right) \tag{3}$$

2. The endoscope of claim 1, further comprising display means for displaying at least one of the bloodstream amount and the oxygen saturation rate obtained by the calculation means.

3. The endoscope of claim 1, wherein the pickup means includes an optoelectronic device for picking up the picture signals and the the reference picture signals as the correction signals from the object and the reference member, respectively, irradiated with the light beams.

4. The endoscope of claim 1, wherein the reference member is a reference white plate.

5. The endoscope of claim 1, wherein the light beam generating means includes a filter device having a transparent filter member for passing a white light and at least two other filter members for passing light having different wavelengths, a light source for generating the white light to be passed through the filter device, respectively and means for selecting one of the transparent filter member and the two other filter members.

6. The endoscope of claim 1, wherein the light beam generating means includes a light source for generating a white light, a variable wavelength light beam generator for generating at least two other light beams having different wavelengths, and means for selecting one of the white light and the two other light beams.

7. The endoscope of claim 1, wherein the light beam generating means includes a light source for generating a white light, at least two light beam generators for generating light beams having different wavelengths, and means for selecting one of the white light and the two other light beams.

8. An endoscope, comprising:
means for generating light beams of different wavelengths toward an object;
pickup means for picking up picture signals from the object by using the light beam, and also picking up correction signals from a reference member by using the light beams; and
calculation means for calculating a bloodstream amount $I_{HB}$ and an oxygen saturation rate $I_{SO2}$ from the picture signals and the correction signals according to formulas (1), (2) and (3), $$\Delta A_{ij} = \log E\lambda j - \log E\lambda i + bi \ldots \quad (1)$$

wherein $E\lambda i$ and $E\lambda j$ are the picture signals and $\lambda i$ and $\lambda j$ are wavelengths and wherein $bi$ is a constant and $i$ and $j$ are integers 1, 2, 3, 4, ...

$$I_{HB} = 200 \cdot \Delta A_{14} \ldots \quad (2)$$

$$I_{SO2} = 0.673 \cdot \left( \frac{0.45 \cdot \Delta A_{21} + 0.55 \cdot \Delta A_{23}}{\Delta A_{13}} \right) \quad (3)$$

9. The endoscope of claim 8, further comprising display means for displaying at least one of the bloodstream amount and the oxygen saturation rate obtained by the calculation means.

10. The endoscope of claim 8, wherein the pickup means includes an optoelectronic device for picking up the picture signals and reference picture signals as the correction signals from the object and the reference member, respectively, irradiated with the light beams.

11. The endoscope of claim 8, wherein the reference member is a reference white plate.

12. The endoscope of claim 8, wherein the light beam generating means includes a filter device having a transparent filter member for passing a white light and at least two other filter members for passing the light beams having the different wavelengths, respectively, a light source for generating the white light to be passed through the filter device, and means for selecting one of the transparent filter member and the two other filter members.

13. The endoscope of claim 8, wherein the light beam generating means includes a light source for generating a white light, a variable wavelength light beam generator for generating at least two other light beams having different wavelengths, and means for selecting one of the white light and the two other light beams.

14. The endoscope of claim 8, wherein the light beam generating means includes a light source for generating a white light, at least two light beam generators for generating light beams having different wavelengths, and means for selecting one of the white light and the two other light beams.

* * * * *